US010338157B2

(12) United States Patent
de Andrade et al.

(10) Patent No.: US 10,338,157 B2
(45) Date of Patent: Jul. 2, 2019

(54) DETECTION OF BIOMAGNETIC SIGNALS USING QUANTUM DETECTOR ARRAYS

(71) Applicants: Marcio C. de Andrade, San Diego, CA (US); Anna Leese de Escobar, San Diego, CA (US); Brandon J. Wiedemeier, San Diego, CA (US); Jamie R. Lukos, San Diego, CA (US); Shannon Kasa, San Diego, CA (US); Matthew A. Yanagi, Jamul, CA (US)

(72) Inventors: Marcio C. de Andrade, San Diego, CA (US); Anna Leese de Escobar, San Diego, CA (US); Brandon J. Wiedemeier, San Diego, CA (US); Jamie R. Lukos, San Diego, CA (US); Shannon Kasa, San Diego, CA (US); Matthew A. Yanagi, Jamul, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/980,969

(22) Filed: May 16, 2018

(65) Prior Publication Data
US 2018/0267116 A1 Sep. 20, 2018

Related U.S. Application Data

(63) Continuation-in-part of application No. 15/360,323, filed on Nov. 23, 2016, now Pat. No. 10,234,514.

(51) Int. Cl.
*H01Q 1/36* (2006.01)
*G01R 33/035* (2006.01)
*A61B 5/04* (2006.01)

(52) U.S. Cl.
CPC ...... *G01R 33/0354* (2013.01); *A61B 5/04008* (2013.01); *G01R 33/035* (2013.01); *H01Q 1/364* (2013.01)

(58) Field of Classification Search
CPC .. H01Q 1/364; G01R 33/035; G01R 33/0354; A61B 5/04008
See application file for complete search history.

(56) References Cited

U.S. PATENT DOCUMENTS 5,601,081 A  2/1997 Tomita et al.
6,363,268 B1  3/2002 Schuchardt et al.
(Continued)

OTHER PUBLICATIONS

Fagaly, R.L., "Superconducting Quantum Interference Device Instruments and Applications", Rev. Sci. Instrum., 77, 101101 (2006).
(Continued)

*Primary Examiner* — Graham P Smith
(74) *Attorney, Agent, or Firm* — NavInfWarCen Pacific; Arthur K. Samora; Kyle Eppele (57) ABSTRACT

A biosignal measuring device that can include at least one Super-conducting Quantum Interference Device (SQUID) array (SQA) of High Temperature Superconducting (HTS) Josephson Junctions (JJs). The HTS JJs operating parameters can be adjusted to establish an anti-peak response for the SQA, that can be at a maximum along a defined response axis, for detection of extremely small biomagnetic fields. For operation, the SQA can be maneuvered around a target area of a stationary subject that is emitting biomagnetic signals using a stand with three degrees of freedom, so that the response axis remains orthogonal to the subject target area. The device can further include a radome with an atomic layer deposition (ALD) window on the radome surface. The radome ALD surface can allow for passage of magnetic signals through the ALD window and radome, while simul-
(Continued)

taneously preventing passage of infrared radiation therethrough.

20 Claims, 6 Drawing Sheets

(56) References Cited

U.S. PATENT DOCUMENTS

| | | |
|---|---|---|
| 6,544,170 B1 | 4/2003 | Kajihara et al. |
| 6,690,162 B1 | 2/2004 | Schopohl et al. |
| 7,369,093 B2 | 5/2008 | Oppenlander et al. |

OTHER PUBLICATIONS

Hämäläinen, M., et al., "Magnetoencephalography—Theory, Instrumentation, and Applications to Noninvasive Studies of the Working Human Brain", Reviews of Modem Physics, 65(2), 413 (1993).

Häussler, C., Oppenländer, J., & Schopohl, N., "Nonperiodic Flux to Voltage Conversion of Series Arrays of DC Superconducting Quantum Interference Devices", Journal of Applied Physics, 89(3), 1875-1879 (2001).

Leahy, R. M., Mosher, J. C., Spencer, M. E., Huang, M. X., & Lewine, J. D., "A Study of Dipole Localization Accuracy for MEG and EEG Using a Human Skull Phantom", Electroencephalography and Clinical Neurophysiology, 107(2), 159-173 (1998).

Minassian, B. A., Otsubo, H., Weiss, S., Elliott, I., Rutka, J. T., & Snead, O. C., "Magnetoencephalographic Localization in Pediatric Epilepsy Surgery: Comparison With Invasive Intracranial Electroencephalography", Annals of Neurology, 46(4), 627-633 (1999).

Mitchell, E. E. and Foley, C. P., "YBCO Step-Edge Junctions With High IcRn", Supercond. Sci. Technol. 23, 065007 (2010).

L. L. Sohn, M. T. Tuominen, M. S. Rzchowski, J. U. Free, and M. Tinkham, "AC and DC Properties of Josephson—Junction Arrays With Long-Range Interaction", Phys. Rev. B., Condens Matter, vol. 47, No. 2, pp. 975-984 (Jan. 1993).

VRBA, J. et al., "Whole Cortex, 64 Channel SQUID Biomagnetometer System", IEEE Transactions on Applied Superconductivity, vol. 3, No. 1 (Mar. 1993).

Elekta Neoromag® TRiUX Magnetoenciphalography Device Brochure, 2011.

Lukos, J. et al., "Towards a Portable Magnetoencephalography (MEG) Device", Poster, Office of Naval Research Science & Technolgoy Expo Jul. 20-21, 2017, and Medical Health System Research Symposium (MHSRS) Aug. 27-30, 2017.

DETECTION OF BIOMAGNETIC SIGNALS USING QUANTUM DETECTOR ARRAYS

CROSS REFERENCE TO RELATED APPLICATIONS

This application is a continuation-in-part of U.S. patent application Ser. No. 15/360,323, filed Nov. 23, 2016, by Anna Leese de Escobar et al., entitled "System and Method for Controlled, And Selective, Broadband Far and Near Field Radio Frequency Radiation Detector Utilizing Superconducting Quantum Detector Arrays". The contents of the '323 application are hereby incorporated by reference into this specification.

FEDERALLY-SPONSORED RESEARCH AND DEVELOPMENT

The United States Government has ownership rights in this detector. Licensing and technical inquiries may be directed to the Office of Research and Technical Applications, Space and Naval Warfare Systems Center, Pacific, Code 72120, San Diego, Calif., 92152; voice (619) 553-5118; ssc_pac_t2@navy.mil. Reference Navy Case Number 104962.

FIELD OF THE INVENTION

This invention pertains generally to magnetic field sensors. More particularly, the invention pertains to sensors that leverage cryogenics and quantum sensor technology to develop a portable biomagnetic signal detection device to measure biomagnetic responses from organic organisms using High Temperature Superconducting (HTS) arrays of Josephson junctions (JJs) that can be fabricated in the form of Superconducting Quantum Interference Device (SQUID) arrays. The invention is particularly, but not exclusively, used as a biomagnetic signal detection for taking non-invasive brain images.

BACKGROUND OF THE INVENTION

Superconducting Quantum Interference Device (SQUID) arrays have been proposed in the prior art for utilization as radio frequency (RF) magnetic field detectors and as low noise amplifiers for existing primary antenna structures. These arrays of SQUIDs, which can be connected in a plurality of ways, are also known as Superconducting Quantum Interference Filters (SQIFs) or Superconducting SQUID arrays (SQAs). SQAs can consist of Josephson Junctions (JJs), or any other arrays of elements based on superconductivity that provide constructive interference patterns between the elements. Individual Josephson junctions can also be utilized. However, there is no known way to provide a seamless solution for a system consisting of a SQIF chip (i.e., an SQA) in conjunction with supporting structures that can allow for obtaining a calibrated transfer function for the broadband information carried by free space electromagnetic waves.

Being able to accurately detect the magnetic fields that are generated by living organisms' physiological activity with high spatial and temporal resolution can be critical to effectively diagnosing and understanding the physiological activity. For example, very sensitive magnetic field sensors can be used to detect and localize neurological disorders, traumatic brain injuries and understanding human cognition among other use cases is an application for. One such biomagnetic sensing device can be a noninvasive brain imaging technique that measures the magnetic field changes caused by neuronal firing in the brain. This can be a very valuable tool for imaging, because it can be capable of providing sub-millisecond resolution and millimeter cortical accuracy non-invasively.

Similar technologies that measure magnetic fields but use different sensing methods, such as magnetoencephalography (MEG) and Magnetic Resonance Imaging (MRI), are widely accepted as valuable tools in the field of neuroimaging for both research and clinical purposes. A critical advantage of sensing the magnetic fields over other brain imaging techniques, such as EEG, which measures the electric activity, is that magnetic potentials in the brain are not corrupted by muscle movements and physical skull/tissue properties, which can distort cortical electrical signals.

Despite this advantage, MEG and MRI have not increased in popularity to the same extent as other brain imaging modalities, such as electroencephalography (EEG), because the limitations of current MEG systems. These limitations can include rigid sensor placement (which can cause non-optimal signal detection), expensive magnetic shielded rooms to operate effectively, millions of dollars in cost, and lack of portability due to weight and physical form factor.

The intrinsic limitation of current magnetic field biosensors is due to the sensing element, a Superconducting Quantum Interference Device (SQUID), which is typically coupled to a gradiometer and/or magnetometer allowing the detection of magnetic fields as low as 10-15 Tesla (femptoTesla) at millisecond time scales. Typically, the SQUIDs utilized in existing equipment can only operate in highly magnetically shielded environments and at very low temperatures that can require the use of liquid helium as a cryogen. However, the capability to produce Superconducting Quantum Arrays consisting of thousands micro-fabricated SQUIDs circuits operating collectively can allow for operation without the need for massive shielded rooms, while maintaining the sensitivity levels of SQUIDs. Another important difference of SQAs is the flux to voltage transfer coefficient. SQAs can exhibit a substantial higher flux-to-voltage transfer coefficient, which can make it feasible to operate the SQA in unshielded situations. Typically, SQAs can provide far superior broadband characteristics than single SQUIDs (up to 100 GHz), with high dynamic range and linearity.

Experiments in the Cryogenic Exploitation of Radio Frequency (CERF) laboratory of the Department of the Navy, Space and Naval Warfare (SPAWAR) Systems Center, Pacific have demonstrated the unshielded operation of SQUID arrays that can detect frequencies from DC to above 100 MHz. Additionally, the CERF laboratory has recently performed the first demonstration of a SQUID array in the open without any shielding. Furthermore, it was also demonstrated the detection of magnetic signals of any amplification in the front or end. The SQUID arrays used in this demonstration were also specifically fabricated for the purpose to demonstrate the capabilities of SQUID arrays to detect small magnetic fields without amplification and shield.

In addition to the relaxation of the shielding requirement, relaxing of operating temperature restrictions can be fundamental to making the SQUID arrays a viable device for medical applications. To do this, high temperature superconductor (HTS) SQUID arrays, or SQUID arrays that can operate in the temperature range of 75 to 100 degrees Kelvin (75-100° K.) can be used. HTS SQUIDs can be adapted to operate at liquid nitrogen temperatures, which can be much higher (relatively speaking), than traditional liquid helium temperatures of other SQUID arrays. Initial tests indicate that HTS SQUIDs can have similar characteristics to their niobium counterpart SQAs (i.e., unshielded operation, high sensitivity, and broadband operation), but with several advantages.

First, because HTS SQUID arrays reduce any complex logistics that are usually associated with the handling of liquid helium. Second, HTS SQUID arrays can considerably reduce the footprint of the equipment, which can further provide for more maneuverability of the device, and can increase the proximity of the sensor to the brain because the requirements to keep nitrogen in its liquid state are much less onerous than for helium. Because typical magnetic signals generated in the human body can be mathematically represented by a typical magnetic dipole, magnetic dipoles can have a magnitude that drops with the inverse of the cube of the distance from the source. This factor is unique to SQUID arrays made of high temperature superconductors and leads to greater sensitivity to the magnetic properties of cortical regions located deeper in the brain once the distance between the sensor and the source of the signal is reduced by a minimum of 10 times resulting in an increase of signal of a minimum of 1000 times. The reduced footprint allows for movement of the device, to place the device much, much closer to the subject for detection of the field In view of the above, it can be an object of the present invention to provide a device that can be capable of detecting biomagnetic signals. Another object of the present invention can be to provide a MEG device that can detect very small electromagnetic signals emanating from the brain, heart, spinal cord, or other biological systems. Still another object of the present invention can be to provide a device that can detect very small electromagnetic signals emanating from any sized animals, insects, and single or colony of cells in a laboratory set-up. Another object of the present invention can be to provide a device for detecting magnetic field, which has a small magnetic footprint, so that the device can be maneuvered around the subject, instead of vice versa. Still another object of the present invention can be to provide a device that can enable biomagnetic signal detection of brain activity and other physiological measurements at depths, frequencies and time scales far beyond what is currently explored in the fields of Neuroscience using HTS SQUID arrays, in order to provide a more lucid picture of the functionality of biomagnetic pathways in the entire body as well as the brain. Still another object of the present invention can be to provide a device that can be manufactured and deployed in a relatively efficient, cost-effective manner.

SUMMARY OF THE INVENTION

A non-invasive magnetic biosignal measurement device of the present invention according to several embodiments can include a cooler assembly, and a probe housing and radome that can enclose a probe assembly. The probe assembly can include a cold finger that can define an axis. The cold finger can terminate in at least one Superconducting Quantum Interference Device (SQUID) array (SQA) of High Temperature Superconducting (HTS) Josephson Junctions (JJs). The probe housing and radome can cooperate to define a cavity that the probe assembly is located in. A vacuum valve can be connected to the cooler assembly and the probe assembly for establishing a vacuum in the cavity around the probe assembly.

The radome can further have a surface, and a window with a layer or layers of thin metallic films deposited by atomic layer deposition (ALD) or any other thin film deposition method can be included. The radome surface can allow for passage of magnetic signals through the window and radome, while at the same time preventing passage of infrared radiation, conduction and convection therethrough. The thin film layer/layers can also work as a frequency selective media, which can function to attenuate undesired frequency (frequencies), while at the same time allowing the passage of electromagnetic signals at frequency (frequencies) of interest to pass therethrough, for further detection by the SQA.

The HTS JJs can each have a set of operating parameters, and the set of operating parameters for each individual JJ can be adjusted to establish an anti-peak response for the SQA as a whole, that can be at a maximum along a defined response axis. This can allow for detection of biomagnetic fields, which can be extremely small (in the fempto-Tesla range). For operation, the SQA can be oriented using a stand with three degrees of freedom (or as a handheld device on some embodiments) so that the SQIF response axis is orthogonal to the target area of a subject that is emitting biomagnetic signals. The response axis can also be coincident with a longitudinal axis for the cold finger, or it can be perpendicular with the cold finger axis, depending on how many SQA are being used in the probe assembly. The JJs can be made of materials that can have a High-Temperature Superconducting (HTS) operating temperature (75-90° K.), which can obviate the need for extensive thermal radiation shields and can allow for a smaller device footprint, which can call for more convenient movement using the stand, or by hand. It can also allow for the device to be placed much closer to the target area, which can further allow for more detailed observation of the subject biomagnetic signals cited above.

BRIEF DESCRIPTION OF THE DRAWINGS

The novel features of the present invention will be best understood from the accompanying drawings, taken in conjunction with the accompanying description, in which similarly-referenced characters refer to similarly-referenced parts, and in which.

DETAILED DESCRIPTION OF EMBODIMENTS

In brief overview, the method and system described herein consists of a system that can adapt Superconducting Quantum Interference Device (SQUID) arrays (SQAs), which have been previously uniquely designed to operate as an active small electrically broadband superconducting antenna based on detection of quanta of electromagnetic radiation, to detect biomagnetic waves. An embodiment of the detector can include SQAs that can include a front end with a mechanism to control the incoming magnetic field, a thermal management interface, a chip carrier for the sensor with proper functionality to control radiation and provide a clean output of the signal, including channelizer abilities (frequency discrimination) and application specific interfaces. The front end, thermal management interface, and chip carrier can work together as a system that can allow the user to isolate and identify free traveling electromagnetic waves in the far and/or near field region of the sensor.

An embodiment of the detector can consist of an SQA that can be configured to capture the Poynting Vector which is the average power flow per unit time, i.e., energy, of a free traveling electromagnetic wave (such as that generated by a subject) of a magnetic biosignal emanating from a subject, while at the same time minimizing environmental noise. Embodiments can also include supporting structure that can transform information of the electromagnetic wave that has been detected by the SQIF to a proportionate electrical signal.

A sensitive magnetic field detector based on a quantum response, such as e.g., an SQA, or any element that can give rise to a Josephson Effect can be used. The device can include different geometries of the fundamental building blocks of SQAs. A single SQUID re SQUID or bi-SQUID could be used. Or, array designs based on a tight integration of individual SQUID/bi-SQUID cells that share inductances with adjacent cells can be used; the phase dynamics and linearity of the array voltage response is optimized so the non-uniformity in inductances of the bi-SQUIDs (as used in the specification, "SQUID" can mean both SQUID and bi-SQUID, and SQA and SQIF refer to arrays of SQUIDs and can be used interchangeably) produces a pronounced overall zero-field single anti-peak in the voltage response for the overall SQA in a particular direction (the response axis, as described more fully below).

The present invention according to several embodiments can leverage recent advancements in cryogenics and quantum sensor technology to develop a portable biomagnetic signal detection device to measure biomagnetic responses from organic organisms using High Temperature Superconducting (HTS) arrays of Josephson junctions (JJs), which can be fabricated in any geometry. These sensors can be used in a magnetic shielded room, or be engineered with a high dynamic range eliminating the need for shielded rooms. One such device can be the one used for Magneto Encephalography (MEG). Furthermore, because the sensors operate according to several embodiments can operate at temperatures high enough to eliminate the need for multiple heat shield barriers, the present invention can allow for a reduced final distance "d" (described more fully below) between the sensor and the magnetic biosignal source (the subject), which can substantially improve the detection of signals originating at deeper sources and frequencies currently not accessible with existing technology.

Figure 1:
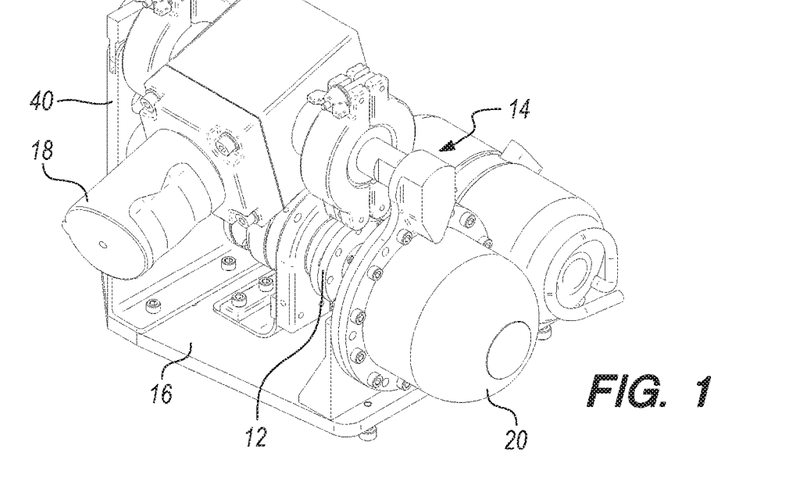
FIG. 1 is a side elevational view of the device of the present invention according to several embodiments.
Figure 2:
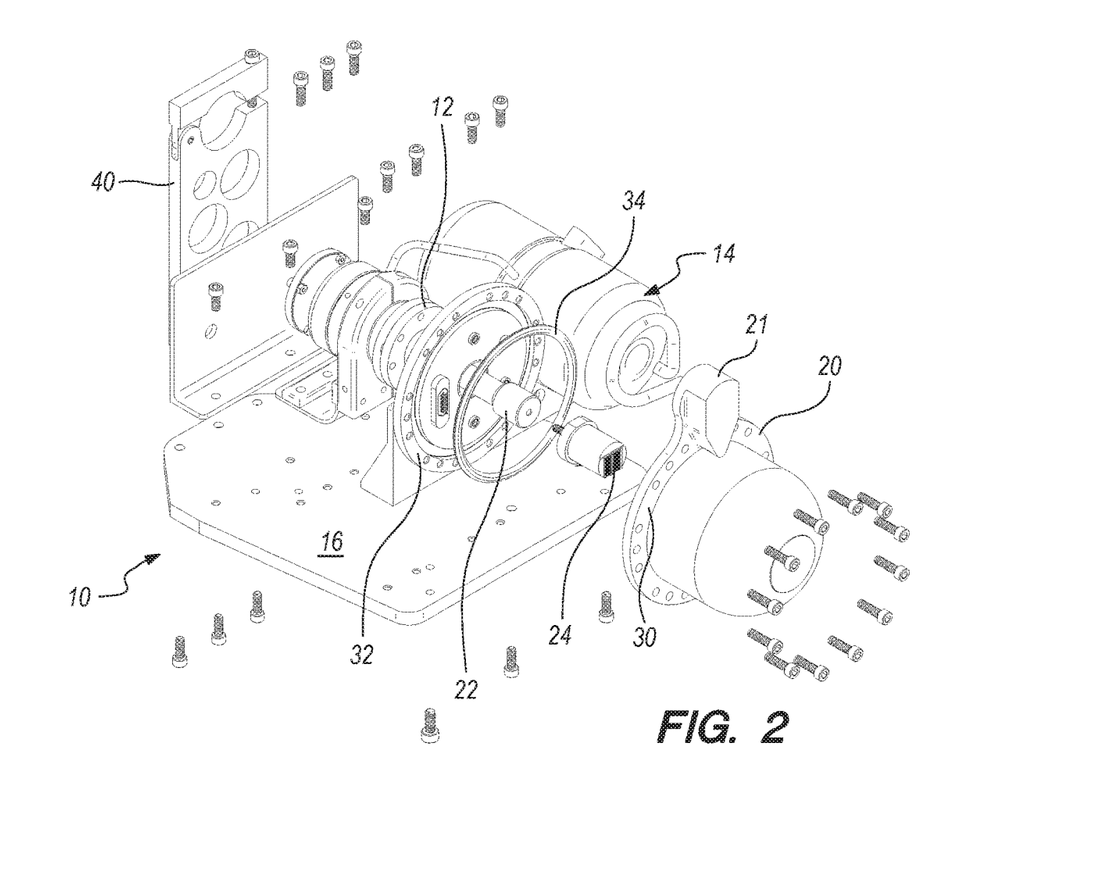
FIG. 2 is an exploded side elevational view, which shows certain components of the device of FIG. 1 in greater detail.

Referring now to FIGS. 1-2, the device of the present invention according to several embodiments can be shown, and can be generally designated using reference character 10. As shown, device 10 can include a probe housing 12 and a cooler assembly 14 that can be mounted to a base 16. A vacuum valve 18 can be connected to cooler assembly 14 and to the distal end of probe housing 12, at radome 20, for establishing a vacuum inside radome 20 during operation of device 10. As shown in FIG. 2, a probe assembly 21 can be situated within probe housing 12. Probe assembly 21 can include a thermal carrier 23 that can be mounted in thermal communication with cold finger 22. At least one Superconducting Quantum Interference Device (SQUID) Array, or SQA 24, can be fixed to thermal carrier 23. SQA 24 can include a plurality of Josephson Junctions, or JJs (The structure of the JJs is too small to be seen in FIGS. 1-2).

The radome 20 can be designed with a transparent cover made out of high-density material. Materials such as DELRIN® or a high-pressure fiberglass laminate composite manufactured to the National Electrical Manufacturers Association standard G-10 can be used to insulate the sensor SQA 24 with a minimal thickness, to allow probe assembly 21 to be placed at a close proximity (as close as twenty millimeters, 20 mm) to the target area 26 of a subject 28 (see FIG. 6). Radome 20 can include an aluminum nitride ceramic insulator on either side of the radome surface to manage temperature. With this configuration, conduction and convection heat transfer will occur to the outer cover (the outer surface of radome 20), while radiation (including biomagnetic radiation) will pass through radome 20 for detection by SQA 24.

Magnetic shielding can be performed using Mu-metal, which is a nickel-iron soft ferromagnetic alloy known in the prior art to have with very high permeability, for shielding sensitive electronic equipment against static or low-frequency magnetic to help absorb ambient magnetic fields. The composition of the Mu-metal can be adjusted to shield ambient magnetic field, while allowing biomagnetic fields to pass through the radome 20 for detection by SQA 24. Note that the fundamental concepts underlying this invention are agnostic to the specific materials identified here, other insulator and shielding materials could be used. Additionally, an atomic layer deposition (ALD) window can be placed on the radome surface. The ALD window can further allow of the passage of magnetic radiation from the subject, while simultaneously blocking ambient magnetic fields, infrared radiation, conduction and convection.

The radome 20 can further function to provide an external vacuum barrier to maintain a vacuum in a cavity 30 defined by probe housing 12 and radome 20, so to assist in isolating SQA 24 from external higher temperatures and to avoid any condensation of gases in the sensor and its surrounding structures. Cold finger 22 can be configured to maintain temperature to below about 9 degrees Kelvin (9° K.) if the JJs material is Niobium, or below about 90° K. if it is a HTS such as Yttrium barium copper oxide (YBCO) and similar rare earth HTS compounds (e.g., DyBaCuO, DY 123, for example) can be used for the JJs. The temperature inside the radome cavity 30 (which can be established when radome 20 is connected to probe housing at flange 32 and gasket 34) can be set to any superconducting temperature that is optimum for that the SQUIDs that are being sued for the SQA. For example, the temperature can be about one hundred and thirty degrees Kelvin (T=130° K.) for mercurybased JJs, or about fifty degrees Kelvin (T=50° K.), for iron-based JJs. The vacuum valve 18, cooling assembly 14 and cold finger 21 can be adjusted to provide temperature adjustments for any SQA operating temperature within cavity transition temperature down to about four degrees Kelvin (T=4° K.); the system can also be modified to achieve even lower temperatures. Subsequently the SQUID array location, together with the engineered PCB board is subject to a vacuum not higher than about $1 \times 10^{-5}$ mbar. The vacuum condition may also be necessary for the reduction of the thermal load on the refrigeration system.

Figure 3:
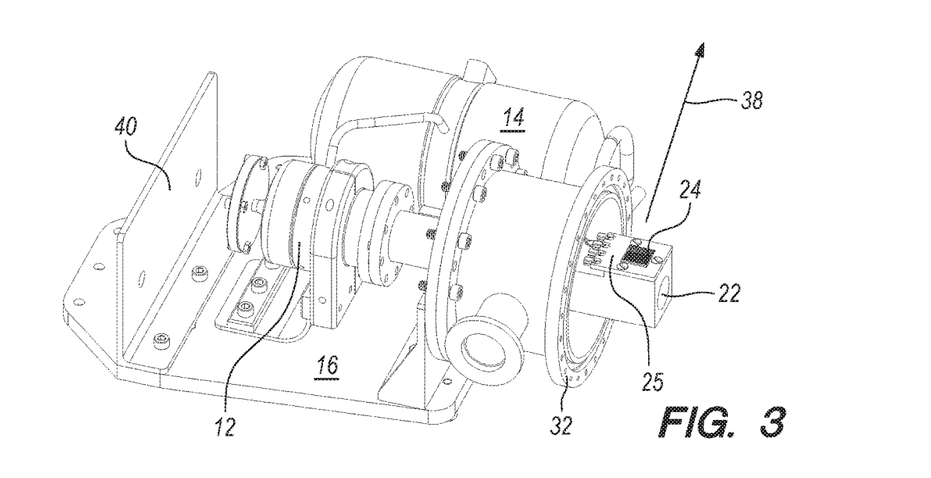
FIG. 3 is the same view as FIG. 1, but with the vacuum valve and radome removed to illustrate the probe assembly Superconducting Quantum Interference Device (SQUID) Array (SQA) in greater clarity and detail.
Figure 4:
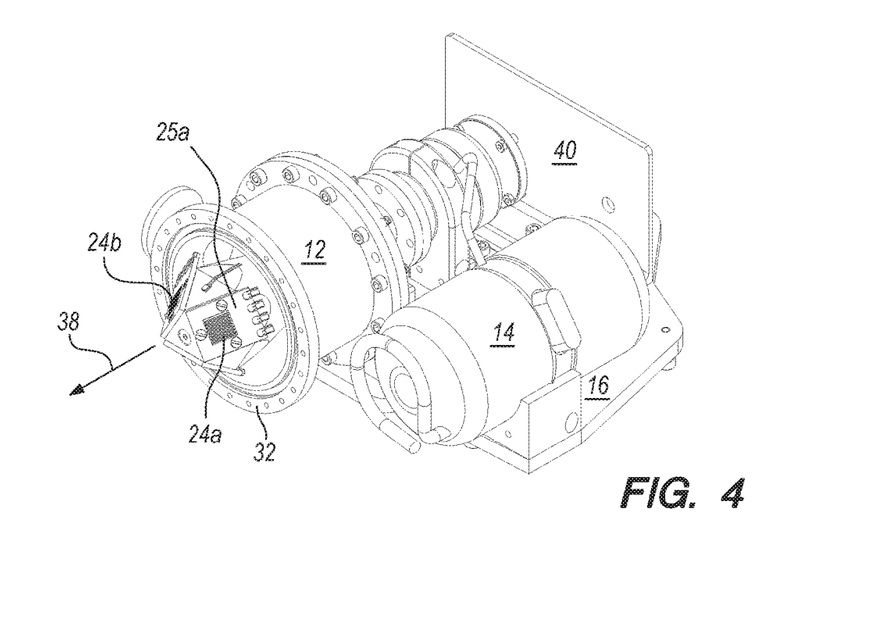
FIG. 4 is the same view as FIG. 3 but for an alternative embodiment of the SQA.

With respect to the SQA 24, and referring now to FIGS. 3-4, The SQUID array chip is mounted to an Aluminum Nitride (ALN) thermal carrier for attachment to cryogenically cooled copper cold finger 22. The thermal carrier 23 and printed circuit board (PCB) 25 can form a permanent test fixture that can wire-bonded with a single SQA 24 located in a cutout at one end of the PCB 25. The combination of all the system's features, i.e., chip, carrier, interface platform, is unique and can allow the SQAs 24 to detect freestanding broadband electromagnetic radiation. Each JJ can have an anti-peak linearity response and a set of operating parameters. The anti-peak linearity and size for each JJ in each SQUID in SQA 24 can be varied to optimize an overall anti-peak response for SQA in a direction along a response axis 38, as shown in FIGS. 3 and 4. To do this, one or more of the operating parameters can be varied. More specifically, multiple SQUID loops can have different combinations of sizes, and can be connected in parallel or in series can be used in the SQA 24. The number of JJs in the SQUIDs can also vary from two to more. For example, a SQUID loop with three JJs can be used as an element of many different loops to form SQA 24. The SQA JJs can also have a plurality of shunt resistors and series resistors between JJs. A serpentine meandering current line 40 can also be included in the array to flux bias the SQUIDs. Other methods for biasing the SQUIDs can be used, particularly in conjunction with SQUIDs that incorporate step edge processes. The bias current and critical current of the JJs can also be varied.

Figure 6:
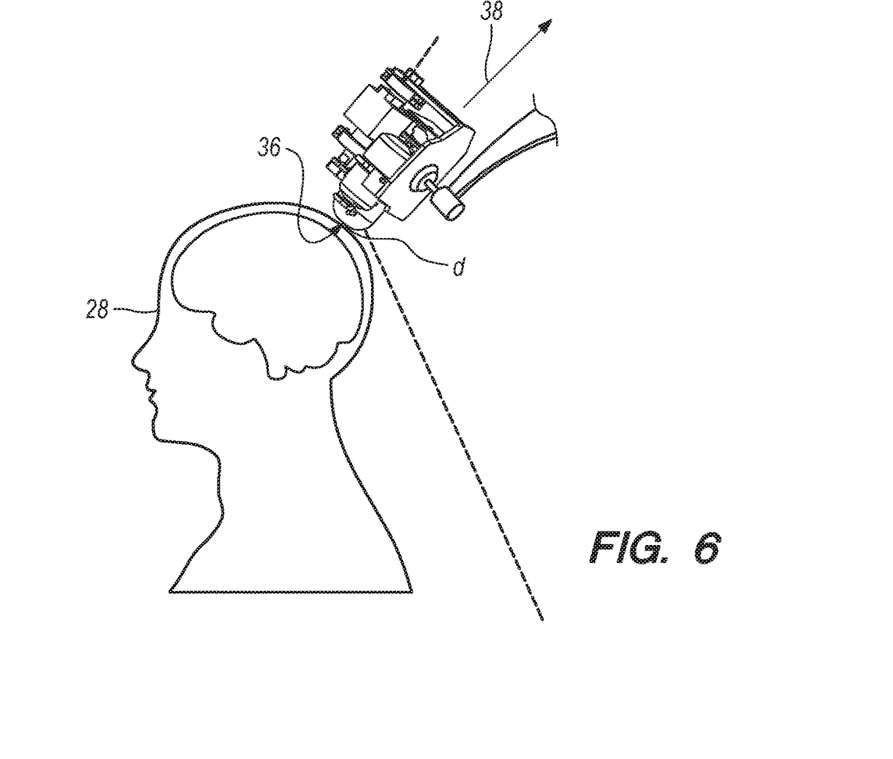
FIG. 6 depicts the device of FIG. 5 during operation.

In addition to the above, the boundary conditions the SQA JJs (which depend on the number, type and spatial orientations of SQA SQUIDs that are used), can be further optimized to maximize the anti-peak response for SQA 24 (and by extension device 10) along the direction of response axis 38 (Please see FIGS. 4 and 6). For example, in the single SQA configuration shown in FIG. 3, the JJ parameters can be adjusted to maximize anti-peak response along a response axis 38 that can be perpendicular to SQA 24. In other embodiments, a two-SQA "steeple" can be used, the JJ parameters can be adjusted to result on an anti-peak response along a response axis 38 that can be coincident with an axis that the cold finger 22 and probe assembly can be centered on. In still other embodiments, and as shown in FIG. 4, a three-SQA "pyramid" configuration can be used, where the JJ parameters can again be adjusted to result on an anti-peak response along a response axis 38 that can be coincident with an axis that the cold finger 22 and probe assembly can be centered on. For this configuration, the potential interaction of the SQA's with each other must also be considered when setting the JJ parameters.

The structure and cooperation of structure of the SQAs, and the operating parameters and manner of adjustment, can be seen and described in greater detail in U.S. patent Ser. No. 15/360,323 by Anna Leese de Escobar for an invention entitled "System and Method for Broadband Far and Near Radio Frequency Radiation Detection Using Superconducting Quantum Detector Arrays. The contents of the '323 application are hereby incorporated by reference herein. The layout implementation of the tight 2D array integration can lead to distinct geometries such as a diamond shape formed by merged dual bi-SQUID cells designed to maximize the energy captured by travelling electromagnetic radiation. To account for boundary conditions, the systems and methods for varying the JJ operating parameters for boundary conditions that was described in U.S. Pat. No. 9,664,751, by Susan Anne Elizabeth Berggren et al. for an invention entitled "2D Arrays of Diamond Shaped Cells Having Multiple Josephson Junctions" can be used. The contents of the '751 patent are hereby incorporated by reference herein. It should be appreciated, however, that different biasing methods could be used, provided an overall anti-peak response for SQIF 24 is obtained along a particular direction (response axis 38).

Still further, The JJ's can be, but are not limited to, superconductor-insulator-superconductor (SIS), superconducting-normal-superconducting SNS, bi-SQUIDs, grain boundary, bi-crystal, step-edge, ramp-edge and ion damage JJs. The SQUID arrays can be composed of any metallic elements such as Niobium, or ceramic elements, such as YBCO and DyBaCuO materials, or any other superconducting material, whether pure metallic, alloy composition, or ceramic. The set of HTS in the $YBa_2Cu_3O_x$ [$6 \leq x \leq 7$] family will also work as materials for the SQUIDs. When the SQUIDs are made of Niobium, the temperature that should be maintained can be nine degrees Kelvin (T=9° K.). Similarly, for SQUIDs of YBCO materials, the temperature that should be maintained can be below about ninety degrees Kelvin (T=90° K.), as the optimum operating temperature would be about seventy-seven degrees Kelvin (T=77° K.). For these embodiments, liquid Nitrogen can be used as the cooling medium instead of liquid Helium, which can be provide further advantages as described below. Still further, other materials can be used to make SQUIDs. For example, the $Nb_3Ge$, Bismuth Strontium Calcium Copper Oxide (BSCCO), the n=2 Bi-2212, $Bi_2Sr_2CaCu_2O_{8+\delta}$, Tl—Ba—Ca—Cu—O families of materials, and other organic superconductors could also be used.

Figure 5:
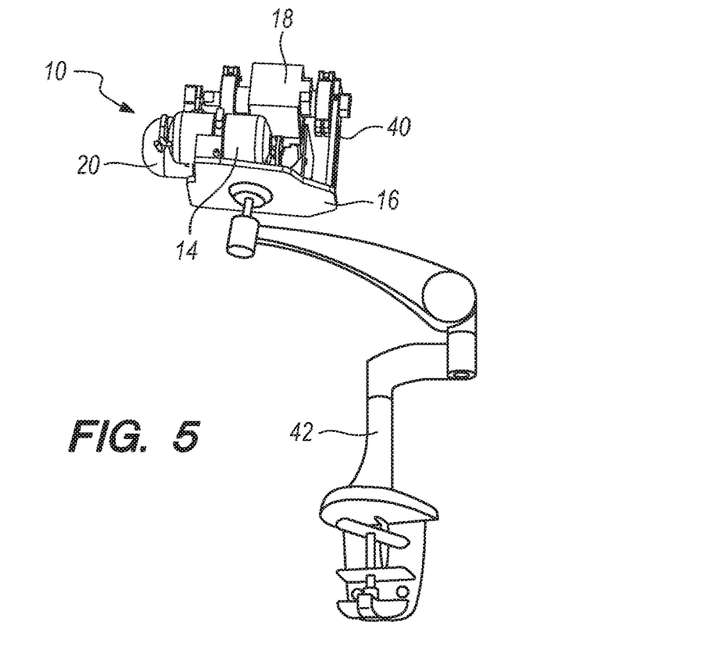
FIG. 5 is a side elevational view of the device of FIG. 1 when mounted to a stand.

As shown in FIGS. 5-6, base 16 and mounting plate 40 of device 10 can be attached to swiveling stand 42. Swiveling stand 42 can have three degrees of freedom, so that when base 16 and mounting plate 40 are fixed to swiveling stand 42, the result can be that device 10 also has three degrees of freedom. Next, device can be moved along the surface of a subject 28 at a distance "d" (FIG. 6), so that the response axis 38 can be orthogonal to a target area 26 of subject 28. As this occurs, the biomagnetic signals of subject 28 can be detected by SQA 24.

For operation of device 10, a bias current versus voltage response (I versus V) can be measured to find the optimum value for the bias current where the SQIF 24 can be superconducting. Once the device bias has been established, the collective response of the SQA 24 can be obtained by introducing a small amount of magnetic flux to the array by flowing a small controlled current in an embedded line within the PCB 25 that is connected to SQA 24. This small amount of magnetic flux can activate SQA 24 and set the SQA 24 into detection mode. Once this process is completed, the SQA 24 and device 10 can be ready to detect incoming electromagnetic radiation. The operation of the device sensor is similar to that described in '323 patent application, where the device can first be calibrated by injecting a small amount of magnetic flux to the SQA after the optimal bias current of the device 10 ("device bias") can be established. This can allow SQA 24 to detect incoming electromagnetic radiation. As shown in FIG. 6, the device probe with calibrated sensor is placed near the area of interest at a distance "d" from target area 26 (such as, but not limited to, the scalp, spinal cord, peripheral nerves, heart, etc.) of subject 28 to record biomagnetic responses.

Referring now to FIGS. 7-12, an alternative handheld embodiment of the device 10 of the present invention can be shown. As shown, device 10 can include a cold finger 22 that can be surrounded by cold finger housing 50. Housing 50 can include an upper portion and a lower portion which can be assembled together, along with seal 69 (FIG. 10) to establish housing 50. A cryo-reservoir 70 can placed within cold finger housing 50 in fluid communication with the interior or cold finger 22 (Please see FIGS. 10-11). The cryo-reservoir 70, housing 50 and cold finger 22 can cooperate to establish, a vacuum around cold finger 22. Housing 50 can be surrounded by inner insulation 52. Outer insulation 54 can surround inner insulation 52. A plurality of non-metallic ties 56 can be used to secure insulation 52, 54 to housing 50 and keep insulation 52, 54 in place. A vacuum connection can establish a vacuum in the annular cavity 30 defined by cold finger housing 50, cold finger 22 and cryo-reservoir 70 using vacuum line 58, which can be inserted through insulation 52, 54 and through housing 50, as perhaps best seen in FIG. 11.

Figure 9:
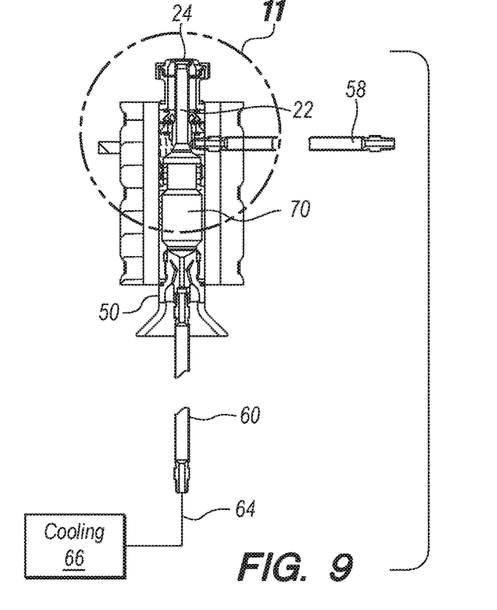
FIG. 9 is a cross-sectional view taken along line 9-9 in FIG. 8.
Figure 10:
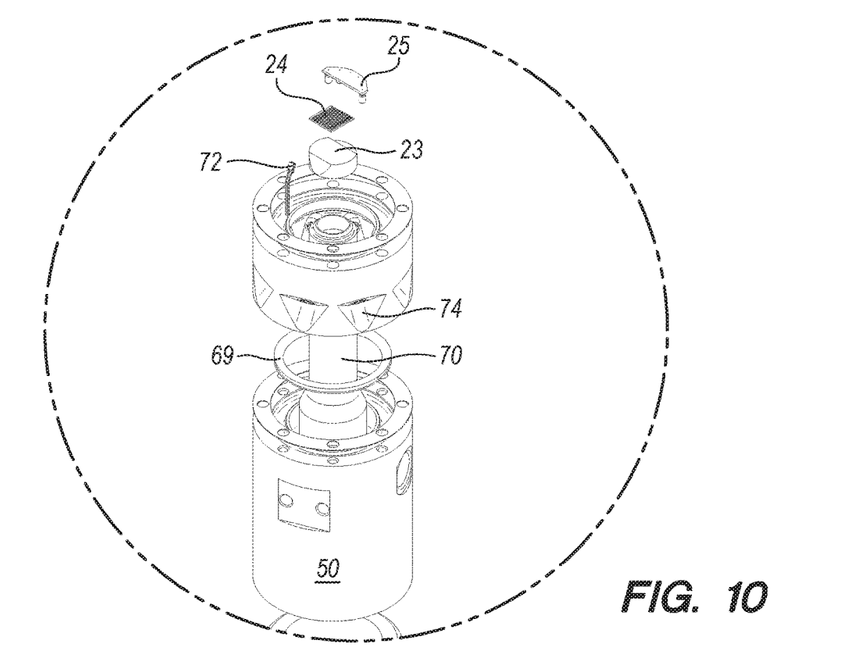
FIG. 10 is an exploded side-elevational view of the components of FIG. 7.
Figure 11:
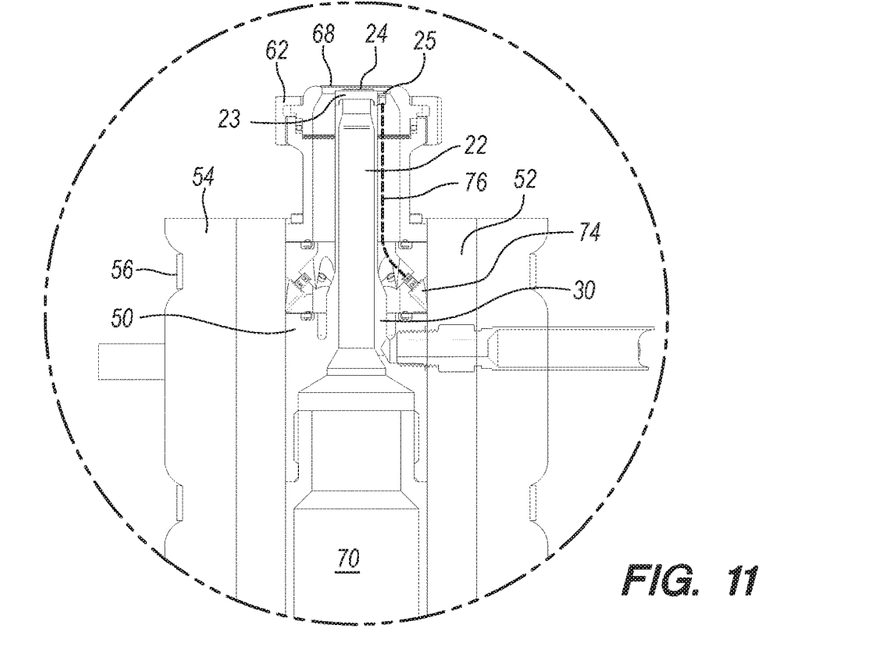
FIG. 11 is an enlarged cross-sectional view taken along line 10-10 in FIG. 9, which can further illustrate the components of FIG. 10 in greater detail.
Figure 12:
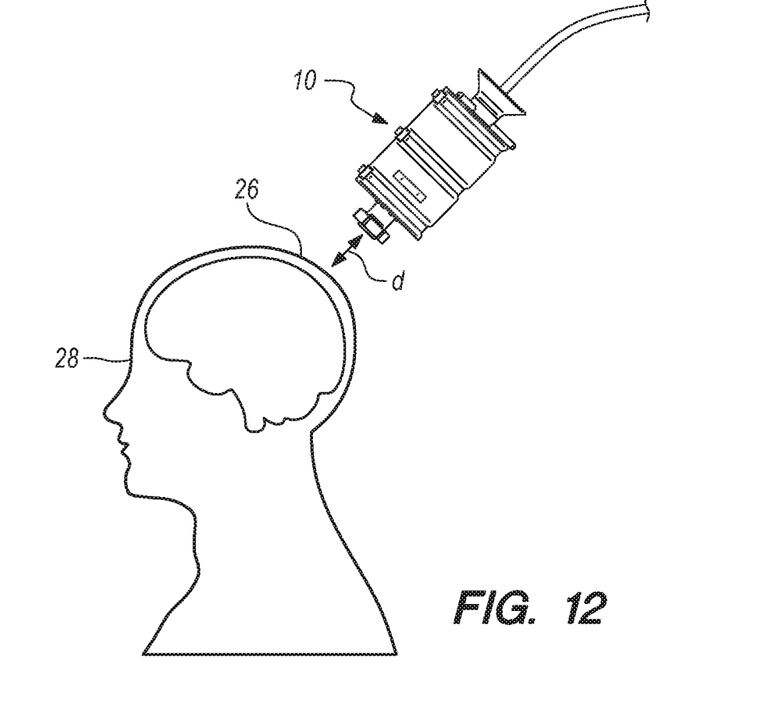
FIG. 12 depicts the device of FIG. 7 during operation.

As shown in FIGS. 10-11, SQA 24 can be inset in thermal communication with thermal carrier 23 (here, a ceramic plate) and cryo-reservoir 70 as described above. Cryo-reservoir 70 can be kept as the desired operating temperature by a cooling line 64. Cooling line 64 can be a braided hose, which can be insulated to minimize heat loss through cooling line 60, and which can be connected to cryogenic cooling medium 66 via a flexible hose type arrangement 64, as shown in FIG. 9. A temperature sensor 72, can also be included to provide feedback as to the actual temperature of cavity 30 (and by extension the temperature of SQA 24). With this configuration, SQA 24 can be maintained at the desired superconducting temperature (which can depend on the SQA type and materials as described above) for operation of the device 10 shown in FIGS. 7-12.

For operation, and referring again to FIGS. 7-12, device 10 can be positioned by hand at a distance "d" from a target area 26 of interest for subject 28 (See FIG. 12). For this embodiment, SQA 24 can be covered by cap 62. It should be appreciated that for this embodiment, the flat surface 68 of cap 62 (Please see FIG. 11) and the handheld nature of the device 10 of FIGS. 7-12 (In FIG. 12, device 10 as shown is not to scale, it is illustrated is being larger for clarity) can allow for placement and maneuvering of device 10 at a lesser distance "d" than for other similar device as known in the prior art. Further, device 10 can be maneuvered around subject 28 to minimize distance "d", instead of vice versa for magnetic biosignal devices of the prior art (i.e. moving subject 28 relative to the prior art device, due to the size and weight of prior art devices). In any case, as biomagnetic signals of interest from subject 28 are detected by SQA 24, the signals can be converted to a usable form by PCB 25, and the routed through conduit 74 via wiring (depicted by dotted line 76 in FIG. 11), for further processing and interpretation by the user.

Figure 13:
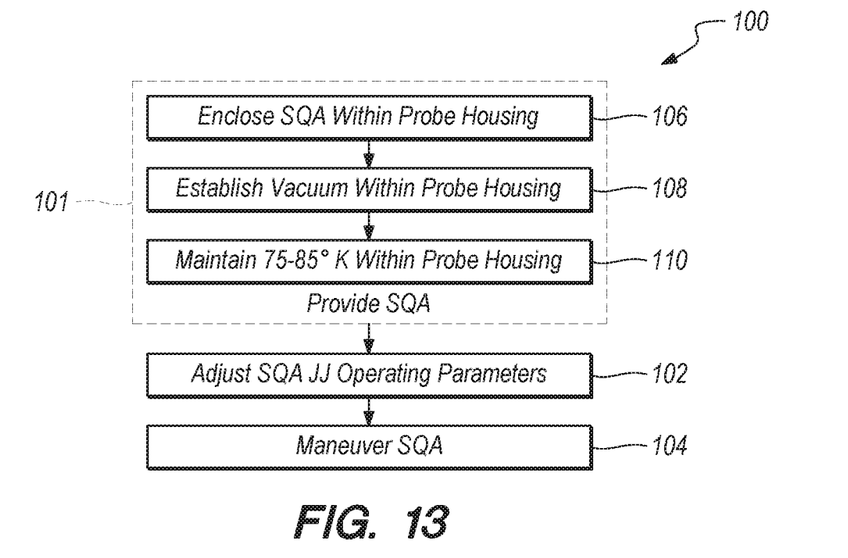
FIG. 13 is a block diagram, which depicts steps that can be taken to accomplish the methods of the present invention according to several embodiments.

Referring now to FIG. 13, a block diagram 100 is shown, which can be used to illustrate the methods of the present invention according to several embodiments. As, method 100 for accomplishing detection of biosignals can include the initial step 101 of providing at least one SQA 24. The SQA can at least one SQA have a plurality of High Temperature Superconducting (HTS) Josephson Junctions (JJs), with each of the HTS having a set of operating parameters. The method 100 can also include the step 102 of adjusting one or more of the set of operating parameters of the HTS JJ's from the SQA(s) 24 to establish a maximum anti-peak response for the SQA(s) along response axis 38. As shown by block 104, the methods according to several embodiments can further include the step of maneuvering the SQA(s) so that said response axis 38 can be orthogonal to a target area 26 of a subject 28 that is generating a signal. One way to accomplish step 104 can be to attached mounting plate 40 and base 16 to a swiveling stand 42 having three degrees of freedom, and moving device 10 around the changing target area 26 of a stationary subject 28, as described above. Other embodiments can include the step of providing multiple, stationary SQAs that can be perpendicular to each other, and then moving subject 28 relative to the SQAs. Other steps could be taken as well.

Figure 7:
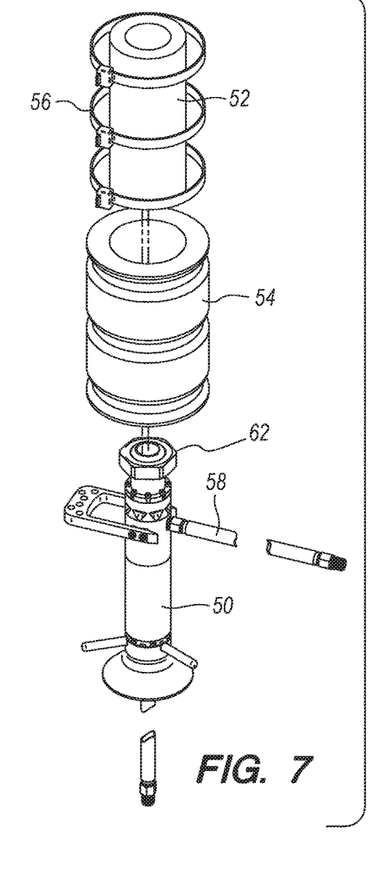
FIG. 7 is an exploded side elevational view of an alternative embodiment of the device of FIG. 1.
Figure 8:
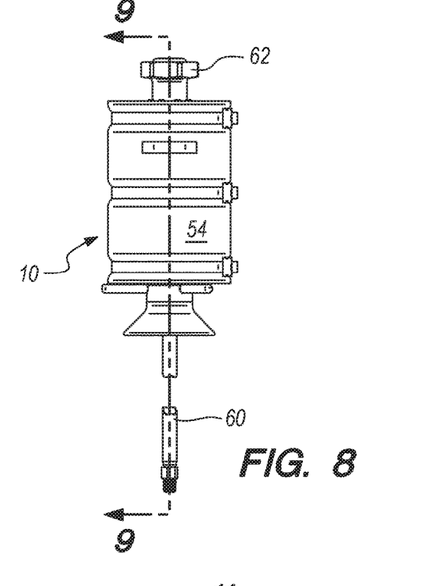
FIG. 8 is a side plan view of the device of FIG. 7.

As shown in FIG. 7, step 101 can further include the step 106 of enclosing the SQA 24 within a cavity 30 defined by probe housing 12 and radome 20, and establishing a vacuum with the defined probe cavity 30, and further maintaining an operating temperature that is commensurate with the step of JJs being used and the manner with which the JJs are arranged and electrically connects. For HTS JJs, the temperature can be maintained at between seventy-five and eighty-five degrees Kelvin (T=75-85° K.) for the probe assembly. Other temperature ranges are certainly possible, depending on the type of JJs that can be used to form SQA 24.

The present invention according to several embodiments can provide several advantages. For example, the device can detect and analyze biomagnetic signals in unshielded environments. The brain's magnetic field generally ranges from 10 to 1000 femptoTeslas ($10$-$10^3$ fT), which is much smaller than the magnetic fields that can typically be found in the ambient environment (~$10^8$ fT). This difference in signal strength has been a pervasive limitation of biomagnetic technologies, resulting in the need for heavily shielded rooms that block environmental interference. The current invention mitigates this issue using the device bias calibration technique described above. An additional important feature of the SQA 24 can be its ability to operate across an extremely wide band of frequencies, potentially up to 100 GHz or higher. This will allow for the search of biomagnetic signals in new regimes of frequency, which may result in detection of previously undetectable biomagnetic signals by the device 10 of the present invention according to several embodiments.

The device can further afford portability advantages that are not known in the prior art for electromagnetic bio imaging devices. This can be because the ability to record signals in an unshielded environment as described can alleviate some restrictions on the mobility of bio imaging systems. Additionally, because HTS SQAs only need to cool down to liquid Nitrogen temperatures (T=77° K.), the required cooling device (and associated size, weight and power requirements) footprints is much smaller than current SQUID sensors that require cooling to liquid Helium temperatures (T=4° K.). The combination of these novel features allows this invention to take a system that is traditionally housed in a large room and enables its portability and use in a much boarder application space (e.g., movement of sensor to different areas of the body), in more real-world settings (e.g., a patient supine due to injury), and scalable to larger populations (e.g., hospitals, research laboratories, etc.).

Still further, the structure and cooperation of structure of the device and methods can allow for much closer position of SQA to the skin (target area 26) of subject 28. The relaxed temperature constraints of the HTS SQAs compared to the traditional SQUID also allow the sensor to be placed much closer to the skin (within twenty millimeters, 20 mm, of target area 26 of subject 28), since a large cooling bath between the sensor and the external interface is not necessary. This change in device architecture will allow this invention to detect cortical and other subcutaneous recordings from much deeper in the brain and body than is currently feasible. This could have far-reaching implications in both clinical and research settings.

The sensor may also act as an active stimulation device for neuromodulatory purposes, similar to transcranial magnetic stimulation (TMS), repetitive transcranial magnetic stimulation (rTMS), peripheral magnetic stimulation (PMS) or repetitive peripheral magnetic stimulation (rPMS). Currently, non-invasive neural stimulation can be accomplished through rTMS and tDCS, which work by inducing or directly exciting electrical currents in brain tissue. These currents have a polarizing or depolarizing effect on neurons. Typically, rTMS involve a coil or pair of coils placed over the head, and tDCS uses electrodes placed on the skin, and both have the proven ability to target specific brain regions with spatial resolution larger than 1 cm$^3$. The primary challenge in stimulating somatosensory feedback is the ability to achieve 1 mm3 spatial resolution at a depth greater than 1 cm below the surface of the scalp. Magnetic stimulation has a trade-off between focality and penetration depth. In general, the smallest possible focal spot is on the order of the depth of interest, so the smallest surface that can be targeted 1 cm below the scalp is about 1 cm$^2$. The device and method according to several embodiments may be able to overcome these and similar challenges.

The present invention according to several embodiments can extend the concept of broadband quantum detection by superconductor SQA devices to result in a device that can be capable of detecting biomagnetic signals. The patentable aspect of this invention stems from the ability to redesign the sensor capabilities to detect very small electromagnetic signals emanating from the brain, heart, spinal cord, or other biological systems. Translating SQUID/SQA technology for near and far field radiation as described above can enable biomagnetic signal detection of brain activity and other physiological measurements at depths, frequencies and time scales far beyond what is currently explored in the fields of neuroscience. Being able to measure this unexplored spectrum could provide a more lucid picture of the functionality of biomagnetic pathways in the entire body as well as the brain.

The devices and methods of the present invention can include several alternative embodiments. More specifically, two levels of specificity of surface selectivity for embodiment of the detector described immediately above configured to interact with a radiation source configured to expose the sample to controlled broadband electromagnetic radiation in the various frequency ranges, to maintain the sample under the controlled temperatures while the sample is exposed to the broadband electromagnetic radiation. The device can utilize SQUID arrays as collectors of magnetic flux as an element of a non-destructive magnetic measurement system, including, but not limited to magnetic microscopes, geophysical magnetometers and biomagnetometers.

The use of the terms "a" and "an" and "the" and similar references in the context of describing the invention (especially in the context of the following claims) is to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A biosignal measurement device comprising:
a cooler assembly;
a probe assembly;
a probe housing and a radome enclosing said probe assembly
a vacuum valve connected to said cooler assembly and said probe housing, said vacuum valve establishing a vacuum in said probe housing; and,
said probe assembly including a cold finger defining an axis, said cold finger terminating in at least one Superconducting Quantum Interference Device (SQUID) array (SQA) of High Temperature Superconducting (HTS) Josephson Junctions (JJs).

2. The device of claim 1, wherein said radome has a surface and an atomic layer deposition (ALD) window on said surface, said ALD surface allowing for passage of magnetic signals through said ALD window and said radome, while preventing passage of infrared radiation therethrough.

3. The device of claim 1, wherein each of said JJ's has a set of operating parameters, and said set of operating parameters are adjusted to establish a maximum anti-peak response in a direction that defines a response axis.

4. The device of claim 1, wherein said device has one said SQA array and said response axis is perpendicular to said cold finger axis.

5. The device of claim 3, wherein said device has two said SQA Arrays in a steeple configuration and said response axis for said steeple configuration is coincident with said cold finger axis.

6. The device of claim 3, where said device has three said SQA Arrays in a pyramid configuration and said response axis for said pyramid configuration is coincident with said cold finger axis.

7. The device of claim 6, further comprising a swiveling stand, said stand having three degrees of freedom for orienting said SQA so that said response axis is orthogonal to a target area of a subject that is generating biomagnetic signals, for noninvasive detection of said biomagnetic signals.

8. The device of claim 6, wherein said device has an operating temperature, and said operating temperature is configured to allow for placement of said radome within twenty millimeters (20 mm) of said target area using said stand to allow for detection of said bio magnetic signals in the 1-10,000 fempto-Teslas ($10^0$-$10^4$ fT) range.

9. The device of claim 8, wherein said HTS JJs are made of a YBCO material.

10. The device of claim 9, wherein said cooing assembly has a liquid Nitrogen cooling medium.

11. A device comprising:
   at least one plurality of High Temperature Superconducting (HTS) Josephson Junctions (JJs), said at least one HTS JJ plurality establishing at least one Superconducting Quantum Interference Device (SQUID) array (SQA);
   a means for maintaining an operating temperature for said at least one HTS JJ plurality in the HTS temperature range; and,
   a means for shielding said shielding said at least one SQA from infrared radiation, while allowing passage of said magnetic fields therethrough.

12. The device of claim 11, wherein said HTS temperature range is between 75 and 90 degrees Kelvin (75-90° K.).

13. The device of claim 11, wherein said shielding means comprises a radome that is attached to said device so that said radome is positioned between said at least one SQA and a target area of a subject that is emitting said magnetic fields, said radome having an inner and an outer surface, and further comprising an atomic layer deposition (ALD) window on one of said inner surface and outer surface.

14. The device of claim 11, wherein said magnetic fields are in the fempto-Tesla range, between 1-10,000 fempto-Teslas ($10^0$-$10^4$ fT).

15. The device of claim 11, wherein said each of said JJ's in said at least one SQA has a set of operating parameters, and each of said set of operating parameters are adjusted to establish an overall maximum anti-peak response for said at least one SQA in a direction that defines a response axis.

16. The device of claim 15 further comprising a means for maneuvering said device so that said response axis is orthogonal to a target area of a subject emitting said magnetic fields as a biomagnetic response.

17. A biosignal measuring method comprising the steps of:
   A) providing at least one at least one Superconducting Quantum Interference Device (SQUID) array (SQA), said at least one SQA having a plurality of High Temperature Superconducting (HTS) Josephson Junctions (JJs), each of said JJ's in said at least one HTS JJ plurality having a set of operating parameters;
   B) adjusting each said set of operating parameters to establish a maximum anti-peak response for said SQA along a response axis; and,
   C) maneuvering said at least one SQA so that said response axis is orthogonal to a target area of a subject generating a biosignal.

18. The method of claim 17, wherein said step C) is accomplished using a device having three degrees of freedom.

19. The method of claim 17 wherein said step A further comprise the steps of:
   A1) enclosing said at least one SQA within a probe housing and a radome, said probe housing and said radome defining a probe cavity;
   A2) establishing a vacuum with said probe cavity; and,
   A3) maintaining an operating temperature of between 75-90° K. within said probe cavity.

20. The method of claim 19, wherein said step C) is accomplished so that said radome is positioned between said at least one SQA and said target area.

* * * * *